United States Patent [19]

Becker et al.

[11] Patent Number: 4,702,907

[45] Date of Patent: Oct. 27, 1987

[54] PROCESS FOR INDUCING SELECTIVE IMMUNOSUPPRESSION OF ANTIBODIES

[75] Inventors: Carl G. Becker, Manhasset; Tova Francus; Gregory W. Siskind, both of New York, all of N.Y.

[73] Assignee: Cornell Research Foundation, Inc., Ithaca, N.Y.

[21] Appl. No.: 521,765

[22] Filed: Aug. 9, 1983

[51] Int. Cl.$^4$ .................. A61K 39/00; A61K 39/12; A61K 39/02; A61K 39/36

[52] U.S. Cl. ........................... 424/88; 424/89; 424/91; 424/92; 514/2; 514/12; 530/350; 530/362; 530/363; 530/807

[58] Field of Search ............... 260/112 R; 424/88, 91, 424/98

[56] References Cited

U.S. PATENT DOCUMENTS

| | | | |
|---|---|---|---|
| 3,794,630 | 2/1974 | Mullan et al. | 260/112 R |
| 3,825,525 | 7/1974 | Mullan et al. | 260/112 R |
| 3,893,993 | 7/1975 | Mullan et al. | 260/112 R |
| 4,140,679 | 2/1979 | Malley | 260/857 R |
| 4,158,705 | 6/1979 | Malley | 424/91 |
| 4,269,764 | 5/1981 | Patterson et al. | 260/112 R |
| 4,356,170 | 10/1982 | Jennings et al. | 424/92 |

OTHER PUBLICATIONS

Becker et al., *Am J. Path*, vol. 96, pp. 249–254, 1979.
Becker et al., *J. Exp. Med.*, vol. 146(2), 1977, pp. 457–467, "Activation of Factor XII by Tobacco Glycoprotein".

*Primary Examiner*—Thomas G. Wiseman
*Assistant Examiner*—Robin Lyn Teskin
*Attorney, Agent, or Firm*—Sughrue, Mion, Zinn, Macpeak, and Seas

[57] ABSTRACT

By coupling an antigen to a polyphenol derivative the formation of the corresponding antibody can be selectively suppressed by administration thereof to the desired subject.

10 Claims, 7 Drawing Figures

PROCESS FOR INDUCING SELECTIVE IMMUNOSUPPRESSION OF ANTIBODIES

This invention was sponsored by the National Heart, Lung & Blood Institute.

BACKGROUND OF THE INVENTION

The present invention relates to a process for (1) the selective immunosuppression of antibodies of the IgG and IgM classes and (2) selective expression of antibodies of the IgE class.

DESCRIPTION OF THE PRIOR ART

The regulatory mechanisms involved in isotype expression in general, and in the IgE response in particular, are poorly understood. Genetic factors appear to influence the tendency to produce IgE antibodies. T-independent antigens generally do not elicit IgE antibodies while parasite infestation and certain adjuvants seem to preferentially stimulate an IgE response. Animal models of the persisting IgE response which is seen in allergic humans have been achieved through various experimental manipulations which probably inactivate suppressor T-cells.

It has been reported that one-third of normal human subjects give immediate, presumably IgE mediated, wheal and flare skin reactions to tobacco glycoprotein (TGP), a glycoprotein containing rutin-like polyphenol groups, which is purified from cured tobacco leaves. A similar incidence of positive skin tests was observed in smokers and non-smokers. In addition, when neonate rabbits are immunized with TGP their anti-TGP response is restricted to the IgE class. Because of this unusual class preference in the response to TGP and because of its possible importance in the pathogenesis of pulmonary and cardiovascular diseases in human smokers we have studied the response of mice to TGP and reached the present invention.

U.S. Pat. No. 4,140,679 Malley discloses a multivalent complex suitable for blocking allergic reactions comprising (1) at least one Timothy Antigen D fragment of a specified structure, (2) a conjugate having a specified structure or (3) a conjugate having a different specified structure covalently bonded to a protein or peptide by a peptide linkage through a glutathione moiety. This patent also discloses a method of treating allergies comprising injecting one of the above complexes into an individual to inhibit antigen induced histamine release and an injectable composition for blocking allergic reactions containing the above complex. This patent does not suggest coupling to a specific antigen to suppress the synthesis of a specific antibody as per the present invention. Instead, Malley provides a way of blocking reactions mediated by an antibody already synthesized.

SUMMARY OF THE INVENTION

We have discovered that by coupling a desired antigen to a polyphenol the production of the corresponding antibody of the IgG or IgM class to that antigen can be selectively immunosuppressed. Also, immunization with polyphenol-coupled antigens can be used to stimulate preferential expression of IgE antibodies if that is desired.

DESCRIPTION OF PREFERRED EMBODIMENTS

Figure 1A:
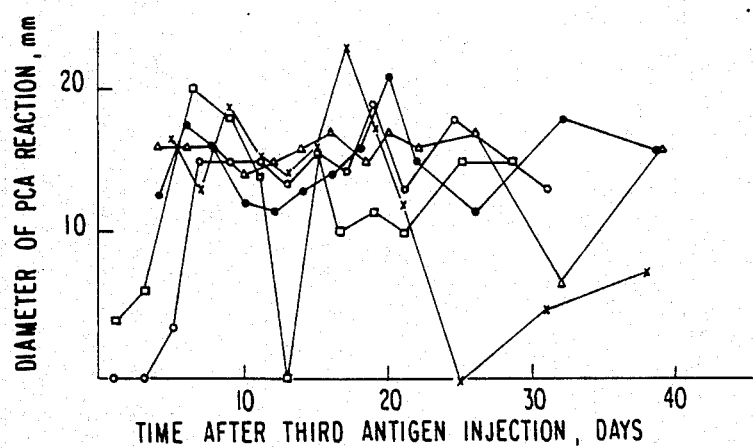
FIGS. 1A, 1B and 1C are plots of diameter of passive cutaneous anaphylaxis reaction in mm versus time after third antigen injection (days) as explained in the specification.

It is known that antigens stimulate antibody production and that, in general, this is important to host defense. However, some diseases are caused by the reaction of autologous or heterologous antigens with specific antibodies. If a means to suppress the production of such specific antibodies could be found, this would be beneficial in the treatment of diseases as discussed below.

For example, a number of different diseases are mediated by deposition of circulating antigen-antibody complexes in and on the walls of blood vessels resulting in inflammation and injury. Such diseases include systemic lupus erythematosus, several forms of glomerulonephritis, rheumatoid arthritis, periarteritis nodosum, certain pulmonary diseases and possibility some of the vascular complications of diabetes mellitus.

In addition, other diseases are mediated by antibodies directed against an antigenic constituent of the body's own tissues or fluids. Such diseases include autoimmune thrombocytopenia where host antibodies are directed against blood platelets, autoimmune glomerulonephritis wherein antibodies are directed against antigens of the renal glomerulus, autoimmune hemoytic anemia, and possibly certain neurologic diseases wherein antibodies may be directed against constituents of nervous tissue.

We propose that when the antigen(s) that react with antibodies to mediate these diseases can be identified and isolated, it could be coupled to rutin or a related polyphenol and the complex used to inject the patent suffering with the disease resulting in suppression of at least IgG and IgM antibodies to that disease with resulting amelioration of signs and symptoms of the disease.

For example, it is known that the immune complexes producing blood vessel injury in systemic lupus erythematosus are composed variably of desoxyribonucleic acid (DNA), ribonucleic acid (RNA), histones, nucleoproteins and antibodies, predominantly IgG and IgM directed against these antigens of which DNA is the most common. In this instance DNA or the other antigens could be coupled to rutin according to the techniques herein and the conjugate used to inject patients to suppress formation of IgG or IgM antibodies and thus the number of circulating immune complexes. It can easily be seen how this strategy could be applied to the other disease states mentioned above, as the responsible antigens are defined.

In another connection there is increasing evidence that production of IgE antibodies against antigens produced by intestinal parasites, especially worms, is important in host defense against these parasites. This is in part because IgE mediated release of tissue mast cells attracts blood eosinophils which are essentially capable of ingesting such parasites. On the other hand, absorption of worm/egg antigens and the formation of circulating complexes of serum antibodies of classes other than IgE and worm antigens might be detrimental to the host. Therefore, limiting the immune response to IgE might be of advantage. Coupling parasite antigens to rutin or related compounds and using these complexes as immunogens would achieve this aim. The advantages of this scheme should be to limit the consequences of parasite infestation to the GI tract and to reduce the severity of infestation by increasing the destruction of the parasite by blood and tissue eosinophils.

The choice of polyphenol or related substance can be wide and can include any phenolic compound with two or more hydroxyl groups attached to it. If only two hydroxyl groups are present they should be in the ortho position to one another. Such a structure would include a large number of naturally occurring aromatic substances that are products of the shikimic acid pathway and/or acetate/shikimate aromatics and acetate/maloriate aromatics (handbook of Naturally Occurring Compounds Vol. I Academic Press, Inc., New York, San Francisco, London, 1975. Devon T.K. and Scott A.I., Eds. pp 4). The structure of rutin is:

Rutin-like moieties are common in nature being present in numerous plants including cocoa, coffee, ragweed, pollen, tobacco and other members of the Solanaceae family. Like TGP, some of these other rutin derivatives have been shown to be capable of activating factor XII dependent pathways. Other chemical determinants which resemble polyphenols and can activate Factor XII dependent pathways and which, in theory, could be coupled to protein or other carriers as in this application are listed in Ratnoff, O. D. and Crum, J. D. J. Lab. Clin. Med. 63:359, 1964, incorporated by reference.

The desired protein antigen can be coupled directly to rutin following activation of the latter by cyanogen bromide. A carbohydrate antigen could be activated with cyanogen bromide and coupled to a basic amino acid or polymer thereof such as lysine or arginine or to a protein. This complex could then be coupled to rutin which had been activated with cyanogen bromide. Alternatively polyphenols (e.g. ellagic acid) which did not have carbohydrate moieties attached as does rutin could be coupled to proteins containing glutamic and/or aspartic acid by incubination together under alkaline conditions, e.g., pH 8.0. In this case hydroxyl groups on the polyphenol would react with carbonyl groups on glutamic and aspartic acid. These substances could also be coupled to proteins as described by Malley. Other coupling procedures are described by Sela, M. and Fuchs, S. in Handbook of Experimental Immunology. Ed. by D. Weir. F. A. Davis Co., Philadelphia, Penna. 1973, Chapters 1 and 11 and by Kabat, E. A. Structural Concepts in Immunology and Immunochemistry, Chapter 2, pages 16–41. Holt, Rinehart and Winston, N.Y., 1976, all incorporated by reference.

Examples of such an application would include

1. Coupling Desoxyribonucleic acid to a protein, lysine, or arginine and then to rutin, using the final complex to induce suppression of anti DNA antibodies.

2. Coupling glomerular basement membrane (GBM) antigen to rutin or another polyphenol, using the final complex to induce suppression of anti GBM antibodies in glomerulonephritis mediated by such antibodies.

3. Coupling blood platelets or platelet antigens to rutin or a related polyphenol, using the final complex to induce suppression of anti platelet antibodies in patients with antibody mediated thrombocytopenia.

4. Coupling erythrocyte antigens (or intact erythrocytes) to polyphenols, using the final complex to induce suppression of antibodies to blood group substances.

5. Coupling hepatitis viral antigens to rutin or related polyphenols and using these complexes to suppress production of antibodies to these proteins in patients with chronic active hepatitis or in patients with periarteritis nodosum associated with hepatitis.

6. Coupling tumor cells or tumor antigens to rutin or related polyphenols, using these final complexes to suppress blocking antibodies to these tumor antigens. These blocking antibodies have been demonstrated in some instances to enhance tumor growth by protecting tumor cells from cell mediated immune defenses.

7. Coupling rutin or a related polyphenol to a tissue antigen such as thyroglobulin; using the final complex to suppress anti thyroglobulin antibodies should result in amelioration of autoimmune thyroiditis.

8. Coupling antigens from intestinal parasites, e.g., protozoans and worms, possibly certain bacteria as well, to rutin or related polyphenols and using these complexes to enhance local production of IgE to these antigens and enhanced phagocytic destruction of these organisms.

Having thus generally described the invention, the following specifically illustrates the same where the following abbreviations are used:

BSA, bovine serum albumin; ELISA, enzyme linked immunoadsorbant assay; F, female; HA, hemagglutination or hemagglutinating; HRBC, human erythrocytes; M, male; PBS, phosphate buffered saline; PCA, passive cutaneous anaphylaxis; PNP, p-nitrophenyl phosphate, disodium; R, Rutin; R-BSA, R conjugated BSA; R-RIg, R conjugated to rabbit immunoglobulin; T, Tween.

Per the later described example, it was found that the repeated intradermal injection of TGP into mice elicited a long lasting specific IgE response but little or no hemagglutinating (HA) antibodies. The presence of rutin moieties on the antigen molecules thus depressed HA antibody production without affecting the IgE response which was confirmed by measuring the IgE and HA antibody responses of mice immunized with bovine serum albumin (BSA) or with a rutin-BSA conjugate (R-BSA). The mice immunized with R-BSA produce IgE antibodies to BSA as did mice immunized with BSA, but the mice immunized with R-BSA produce significantly lower titers of HA antibodies to BSA than do mice immunized with BSA. In addition, an immunization protocol is set forth which elicits a long-lasting, high-titered response of IgE and HA antibodies. The immunization protocol described herein was associated with the described results. However, other protocols relating to dose, route, and spacing of administration might also be effective.

It is generally accepted that the mouse is a reasonable model for the study of immunology and that observations made using mice are relevant to man; this is in part because of the close similarities in structure of the chromosome principally involved in the immune response in mice and men. (Benacerraf, B. and Unanue, E. R. Textbook of Immunology. Chapter 10, pages 178-195, Williams and Wilkins, Baltimore, Md., 1979, incorporated by reference.

When an animal or person is immunized it is assumed that antigen is recognized by cells having receptors for that antigen. Because the immune system is made up of a variety of cell populations the response can be of a "helper" nature, leading to the enhanced production of antibody or of a "suppressor" nature leading to inhibition of antibody production. The data presented herein suggest that when the antigen, like TGP, contains polyphenol haptens the immune response is of a "helper" nature with respect to production of IgE antibodies and "suppressor" with respect to IgG and IgM.

EXAMPLE

Materials And Methods

Animals

Eleven week old male and female LAF1 mice were obtained from the Jackson Laboratories and Sprague-Dawley male rats, 400-450g, were obtained from Charles River Breeding Laboratories (Wilmington, Md.).

Antigens and Antibodies

TCP was isolated from cured tobacco leaves as previously described by Levi, R., Zavecz, J. H., Burke, J. A., and Becker, C. G. (1982) Am. J. Pathol. 106, 318-325. BSA was obtained from Sigma Chemical Company (St. Louis, Mo.) R-BSA, rutin-rabbit immunoglubulin (R-TIg), rabbit anti-TGP serum, and rabbit anti-R-BSA serum were prepared as described by Becker, C. G., and Dubin, T. (1977) J. Exp. Med. 146, 457-467.

HA assay

The HA assay used was as described in the Levi et al article cited. Sera were heat inactivated (56° C. for 30 minutes) prior to assay.

Comparison of R-BSA and BSA by immunoelectrophoretic and HA inhibition assays

The molecular weights of BSA and of R-BSA were estimated by electrophoresis in sodium dodecyl-sulfate polyacrylamide gel per the method of Laemmli, U.K. (1970) Nature (Lond.) 227, 680-685 and were found to be 67,000 and 125,000 daltons, respectively. Therefore, it can be concluded that approximately 95 moles of rutin (M.W. 610) were coupled to one mole of BSA.

Immunoelectrophoresis was used to determine if R-BSA was bound by rabbit antibodies to BSA. BSA and R-BSA at 1 mg/ml were placed in wells and were electrophoresed in 1.5% agarose containing barbital-HCl buffer, pH 8.6, T/2-0.05. Bromphenol blue was added as a tracing dye. After electrophoresis rabbit antiserum was added to BSA in the through. Precipitation acrs of similar density were obtained with both antigens. The distances migrated from the origin by the proteins and the tracking dye were measured, in the case of the proteins from the midpoint of their precipitation arcs, and Rf values were calculated. The Rf value for R-BSA was 0.78; that for BSA was 0.47. The results indicate that conjunction of BSA with rutin brings about an increase in electronegativity but does not impair the capacity of the BSA carrier to be bound by rabbit anti-BSA sera.

The capacity of R-BSA and BSA to inhibit the HA of human erythrocytes (HRBC) coated with BSA by anti-BSA serum was measured. The minimum inhibitory concentration of BSA was 62 ng/ml and of R-BSA was between 36.4 and 72.8 ng/ml.

These observations indicate that rabbit antisera to BSA interact with BSA and R-BSA approximately equally and that conjugation with rutin does not significantly mask the antigenic determinants on BSA. It is consistent with classic observations such as those Kabat and Heidelberger reported in Kabat, E. A. and Heidelberger, M. (1937) J. Exp. Med. 66, 229-250.

Enzyme linked immunoadsorbent assays (ELISA)

The results of HA assays for rabbit and mouse antibody to TGP were confirmed by the ELISA technique per Engvall, E., and Perlmann, P. (1971) Immunochemistry 8, 871-874. Alkaline phosphatase was coupled to goat antibody to mouse IgG which had been purified by $(NH_4)SO_4$ precipitation and affinity chromatography. An alkaline phosphatase conjugate of staphylococcal protein A was a gift from Dr. Peter C. Harpel (Cornell University Medical College).

Wells in polystyrene plates were treated with 50 µl aliquots of serial dilutions of normal mouse serum in 0.1M Na Carbonate—Na Biocarbonate buffer pH 8.9 for 18 hours. The plates were then washed with phosphate buffered saline (PBS) which was 0.1% in Tween 20 (PBS-T). To the wells was added 50 µl of either alkaline phosphatase conjugated goat anti-mouse IgG diluted 1:100 in PBS-T or diluent. The plates were incubated at 37° C. for two hours, were washed and the substrate p-nitrophenyl phosphate, disodium (PNP) (Sigma) in 1M Tris-HCl buffer pH 8 was added. The plates were incubated for 90 minutes, 100 µl of 3N NaOH was added and the optical density was determined (EIA Manual Reader Chromo-Scan, Bio-Tek Instruments, Inc., Burlington, Vt.). The IgG present in 50 µl of a 1:2560 dilution of normal mouse serum (approximately 20 to 40 ng) could be detected.

Wells were similarly treated with TGP at a concentration of 25 µg/ml in coating buffer for 18 hours. The plates were then washed; 50 µl of dilutions of serum from mice immunized with TGP, from normal mice, from rabbits immunized with TGP or from normal rabbits was added; and the plates were incubated for 18 hours at room temperature. Following washing, the plates which had been treated with mouse sera were incubated with alkaline phosphatase conjugated goat-anti-mouse IgG for two hours at 37° C. and plates which had been treated with rabbit sera were incubated with alkaline phosphatase conjugated Staphylococcal protein A for 90 minutes at 37° C. The plates were washed, color was developed and the optical density was determined as described above.

Immunization schedule

LAF$_1$ mice were injected intradermally at four sites with 100 µg of TGP, BSA or R-BSA dissolved in a total of 1 ml of PBS. The mice were boosted twice, at one month intervals, with 100 µg antigen precipitated in 50% alumina (Alhydrogel (Superfos) Accurate Chemical and Scientific Corp., Westbury, N.Y.). The mice were bled from the retroorbital sinus and the sera were stored at −20° C. or −70° C. until used. No loss of reagenic activity was observed even after three cycles of freezing and thawing.

Passive cutaneous anaphylaxis (PCA)

Mouse antisera were assayed for IgE antibodies by PCA per Ovary, Z. (1964) in *Immunol Methods;* C.I.O.M.S. Symposium, ed. Ackroyd, J. (Oxford, Blackwell Scient. Pub.) pp. 259–283 in male Sprague-Dawley rats. Antigen in 2% Evans blue was injected intravenously 72 hours after intradermal injection of appropriately diluted antiserum. PCA titer is the greatest dilution of antiserum which elicits a positive PCA reaction (a blue spot having a diameter $\geq 5$ mm). Heating at 56° C. for one hour resulted in a total loss of PCA activity in all cases.

Results

IgE response to TGP

Twenty-four male and 24 female 11 week old LAF$_1$ mice were injected intradermally with 100 µg TGP in PBS and were boosted one and two months later with TGP precipitated on alum. The mice were bled every other day starting 12 or 36 hours after the second boost. All but four of the 46 surviving mice had IgE antibodies to TGP in their serum two weeks after the second boost. That these PCA reactions were indeed due to IgE antibodies was confirmed by the complete loss of PCA activity after heating the sera for one hour at 56° C. The kinetics of the anti-TGP IgE response was studied in individual male and female mice and is reported in FIG. 1A and Table 1.

Figure 1B:
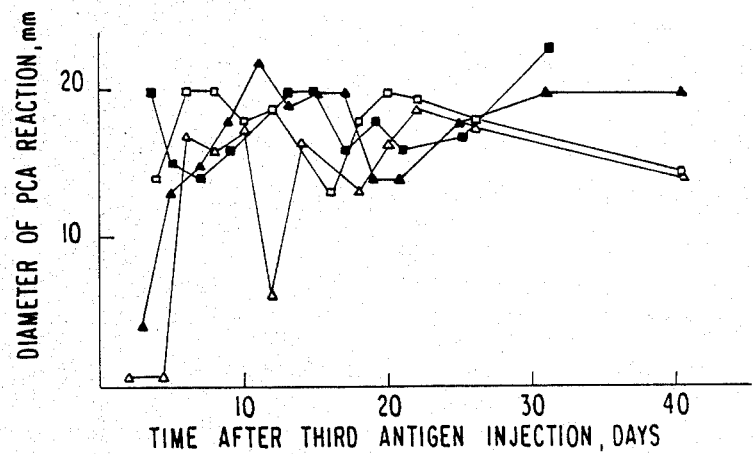
Figure 1C:
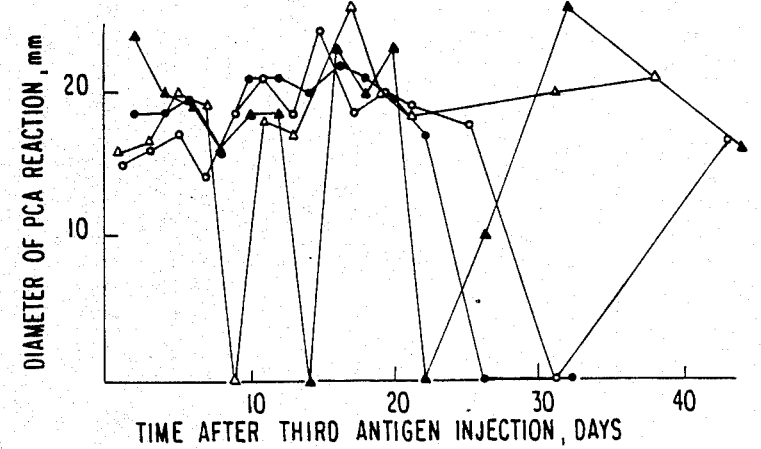

FIG. 1 presents the kinetics of the IgE antibody response of the LAF$_1$ mice immunized by three intradermal injections of TGP, BSA or R-BSA. Sera were diluted 1:25 in PBS and all samples from each mouse were assayed by PCA reaction in an individual rat. The rats were challenged 72 hours after the intradermal injection of antisera with 1 mg of the immunizing antigen injected intravenously in 2% Evans blue. The diameter of the blue spots (measured with calipers) is indicated on the ordinate. The day of bleeding is indicated on the abscissa taking day 0 as the day when the third injection of antigen was given. All samples reported as giving negative PCA reactions were negative when repeated at a 1:5 serum dilution. FIG. 1A represents data on mice immunized with TGP: (●) 40.2, F; (□) 40.13, F; (△) 40.29, M; (O) 40.44, M; (X) 40.47), M. FIG. 1B presents data on mice immunized with BSA: (□) 41.1 F; (■) 41.13, F; (△) 41.27, M; (▲) 41.39, M; FIG. 1C presents data on mice immunized with R-BSA: (●) 42.2, F; (O) 42.13, F; (△) 42.26, M; (▲) 42.39, M.

IgE antibodies to TGP were detectable between one and four days after the second boost and continued to be present, at high titer, for a prolonged time. Seven weeks after the second boost sera from 23 of the 42 surviving mice elicited PCA reactions.

TABLE 1

IgE Antibody Response of Mice to TGP*

| Mice | | PCA titer+ Days after Third Antigen Injection | | | | | |
|---|---|---|---|---|---|---|---|
| No. | Sex † | 7 | 14 | 21 | 26 | 31 | 29 | 45 |
| 40.5 | F | 640 | 640 | 640 | 160 | 160 | N.D.§ | 40 |
| 40.18 | F | 320 | 160 | 160 | 40 | 40 | N.D. | 80 |
| 40.26 | M | 160 | 160 | 80 | 160 | 80 | N.D. | 40 |
| 40.29 | M | 640 | 640 | 640 | 160 | N.D. | 160 | N.D. |

*Mice were given a series of three intradermal injections of 100 µg TGP at monthly intervals: the first dissolved in PBS and the latter two precipitated on alum.
+The PCA titer is defined as the greatest dilution of the antiserum which produces a positive PCA reaction. PCA reactions were elicited with the immunizing antigen.
† F = female; M = male.
§N.D. — not done.

Lack of HA antibodies to TGP in mice immunized with TGP

Sera from mice which were shown to have IgE antibodies to TGP were assayed for their ability to agglutinate HRBC coated with TGP. Since TGP is known to have a rutin-like moiety (see Becker, C. G. and Dubin, T. (1977) *J. Exp. Med.* 146, 457–467), the sera were also assayed for HA antibodies to rutin using R-BSA coated HRBC. As indicated in Table 2, no HA antibodies to TGP or to rutin were detected in any of the sera from mice immunized with TGP. A total of 20 sera obtained from different mice at different times after immunization were studied. It should be noted that the HRBC coupled with TGP or R-BSA were agglutinated by rabbit anti-TGP and rabbit anti-R-BSA, respectively; see Table 2.

TABLE 2

HA Antibody in Sera from Mice Immunized with TGP, BSA or R-BSA*

| Cells Conjugated With | Mouse Anti-TGP | Mouse Anti-R-BSA | Mouse Anti-BSA | Rabbit Anti-TGP | Rabbit Anti-R-BSA | Rabbit Anti-BS |
|---|---|---|---|---|---|---|
| TGP | 0 | 0 | 0 | 200 | 160 | 0 |
| BSA | 0 | 160 | 10,240 | 0 | 10 | 10,240 |
| R-BSA | 0 | tr+ | 0 | 0 | 20 | 2,560 |
| R-RIg | 0 | 0 | 0 | N.D. † | 0 | 0 |
| OVA§ | 0 | 0 | 0 | N.D. | N.D. | 0 |
| No Protein | 0 | 0 | 0 | 0 | 0 | 0 |

*Mouse antisera obtained at different times after immunization with TGP, R-BSA or BSA were studied for their ability to agglutinate HRBC conjugated with the protein indicated. Twenty serum samples were studied for each antigen. Rabbit anti-TGP, rabbit anti-R-BSA and rabbit anti-BSA antisera were included in each assay and served as "positive" controls. Normal mouse serum and normal rabbit serum were included with each assay as controls and were negative in all cases with all of the conjugated HRBC used. Results from a representative assay are presented. A 0 titer indicates no hemagglutination with a 1:10 diluted sample.
+Faint agglutination observed at 1:10 diluted antiserum. Two out of the 20 samples studied exhibited this minimal agglutination, the remaining samples were clearly negative at 1:10 dilution.
† N.D. — not done.
§OVA — ovalbumin.

Lack of IgG antibodies to TGP in mice immunized with TGP

Mouse IgG antibodies to TGP were not detectable by ELISA technique. The ELISA was capable of detecting rabbit IgG antibodies to TGP at dilutions of 1:25,600 to 1:51,200.

Thus, with the immunization schedule employed here, the antibody response to TGP appears to be predominantly or exclusively of the IgE isotype. Furthermore, the IgE response is unusually persistent and of high titer. Whether the unusual characteristics of the immune response of mice to TGP are due to unique properties of the antigen or to the immunization schedule employed was investigated by using BSA and R-BSA as antigens.

IgE response to BSA and to R-BSA

Mice were immunized with BSA or R-BSA using the same protocol as that described above for TGP immunization. The IgE response was similar to that of TGP in that IgE antibodies were detectable three days after the last boost, were present at high titer and persisted for a prolonged period; see FIGS. 1B and 1C, and Table 3. IgE antibodies to BSA and to R-BSA were still present six months after the last injection of antigen at which time 87% (34/39) of the BSA immunized mice and 88% (37/42) of the R-BSA immunized mice had PCA titers of 1:40 or greater; see Table 3.

TABLE 3

IgE Antibody Response by Mice Immunized with BSA or R-BSA*

| Immunogen | Mouse No. | Sex † | PCA Titer+ Days After Third Antigen Injection | | | | | | | |
|---|---|---|---|---|---|---|---|---|---|---|
| | | | 7 | 14 | 19 | 25 | 32 | 41 | 88 | 172 |
| BSA | 41.5 | F | 640 | 1,230 | 320 | N.D.§ | 640 | 320 | N.D. | 80 |
| | 41.13 | F | 640 | 1,280 | 320 | 320 | 320 | 640 | >160 | >160 |
| | 41.25 | M | 640 | 1,280 | 320 | N.D. | N.D. | 320 | N.D. | 20 |
| | 41.42 | M | 640 | 640 | 1,280 | 1,280 | 1,280 | 1,280 | 320 | 80 |
| R-BSA | 42.3 | F | 320 | N.D. | 320 | 320 | N.D. | 160 | N.D. | 80 |
| | 42.16 | F | 320 | 640 | 320 | 320 | 320 | N.D. | 160 | 80 |
| | 42.34 | M | 80 | 320 | 160 | 320 | 80 | 160 | 80 | 40 |
| | 42.37 | M | 320 | 640 | 640 | 320 | N.D. | 320 | 160 | 80 |

*Mice were given a series of three intradermal injections of 100 μg of antigen at monthly intervals: the first dissolved in PBS and the latter two precipitated on alum.
+PCA titer is defined as the greatest dilution of the antiserum which produces a positive PCA reaction. PCA reactions were elicited by the immunizing antigen in each case.
† F = female; M = male.
§N.D. — not done.

Specificity of the IgE antibodies to BSA and to R-BSA

The specificity of the IgE antibodies to BSA and to R-BSA was examined. Rats were sensitized with mouse anti-BSA serum and were challenged 72 hours later with either BSA or R-BSA. Only BSA elicited PCA reactions. Thus the epitopes on BSA recognized by anti-BSA hemagglutinating antibodies are not modified significantly by conjugation of rutin while the epitopes on BSA recognized by the anti-BSA IgE antibodies are modified by the conjugation of the rutin to BSA. On the other hand, both R-BSA and BSA elicited PCA reactions in rats sensitized with mouse anti-R-BSA serum. However, R-RIg did not elicit PCA reactions in sites sensitized with mouse anti-R-BSA serum. The IgE antibodies produced in response to R-BSA thus appear to be mainly specific for epitopes associated with the BSA carrier rather than for the rutin group. Similarly, TGP which contains rutin-like groups, did not elicit a PCA reaction in rats sensitized with IgE anti-R-BSA and R-BSA failed to elicit a PCA reaction in rats sensitized with serum from mice immunized with TGP, suggesting again that the rutin-like group is not a major antigenic determinant. Comparison of the ability of BSA and R-BSA to elicit PCA reactions in rats sensitized with mouse anti-R-BSA serum indicates that the titer obtained with BSA challenge is somewhat lower, as compared with that obtained upon challenge with the immunizing antigen, R-BSA; see FIG. 2B.

Figure 2A:
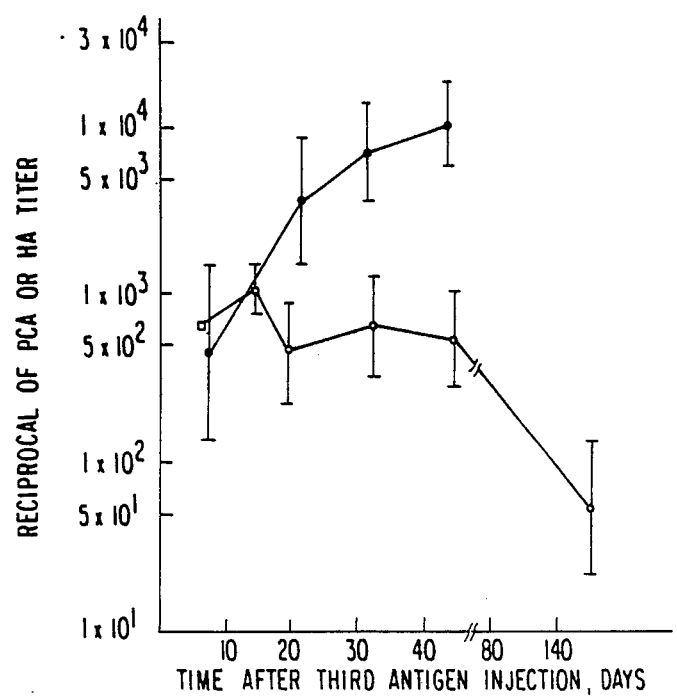
FIGS. 2A and 2B are plots of the reciprocal of passive cutaneous anaphylaxis and hemagglutination titer versus time after third antigen injection (days) as explained in the specification.
Figure 2B:
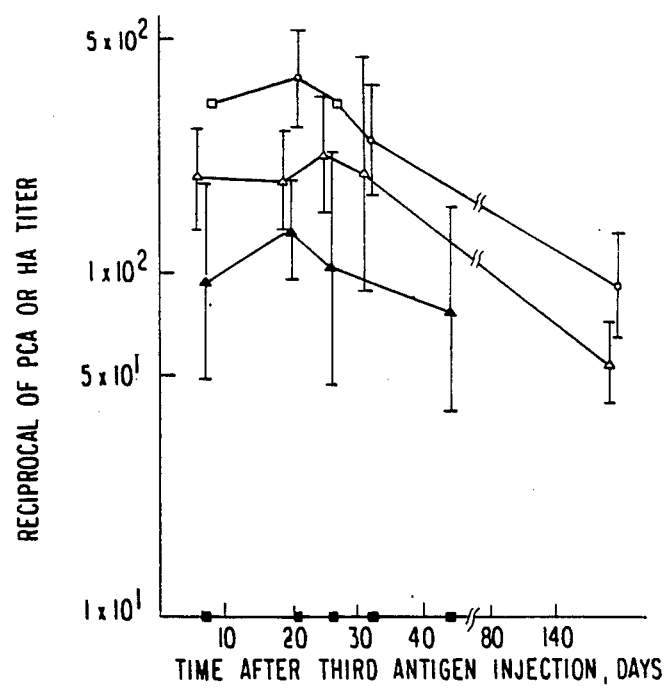

In FIG. 2 HA and PCA titers of sera from the LAF$_1$ mice immunized by three intradermal injections of BSA or R-BSA are presented. The day of bleeding is indicated on the abscissa taking day 0 as the day when the third injection of antigen was given. The reciprocal of the HA or PCA titer is presented on the ordinate. The data are given as a geometric mean and as a standard deviation of the mean for groups of 4 to 5 individual mice. FIG. 2A presents data on mice immunized with BSA: (●) HA titer to BSA-HRBC, (O) PCA titer to BSA. FIG. 2B presents data on mice immunized with R-BSA: (▲) HA titer to BSA-HRBC, (Δ) PCA titer to BSA, (□) HA titer to R-BSA-HRBC, (■) PCA titer to R-BSA.

Production of HA antibodies by mice immunized with BSA

Figure 3A:
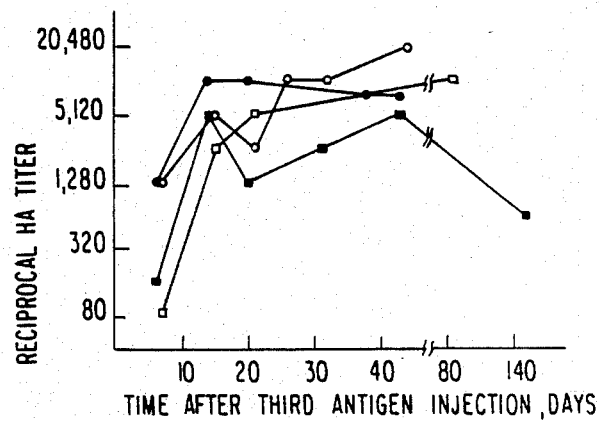
FIGS. 3A and 3B are plots of the reciprocal of hemagglutination titer versus time after third antigen injection (days) as explained in the specification.

The data presented in Table 2, FIG. 2A and FIG. 3A show that the mice immunized with BSA as described above produce HA antibodies to BSA in addition to IgE antibodies. HA antibodies are present five days after the final boost (the earliest time tested), and their titer rises over the succeeding few days and remains high (1:2180 to 1:10,240) for at least three months.

Production of HA antibodies by mice immunized with R-BSA

Sera of mice immunized with R-BSA were assayed for HA antibodies to R-BSA, to rutin and to BSA using HRBC coupled with the appropriate antigen. No HA antibodies to rutin were detected in any of the 20 sera assayed; see Table 2. HA antibodies to the R-BSA conjugate were detected in only two of the 20 sera studied and in those antisera only a faint agglutination was observed at 1:10 dilution; see Table 2. Only low titers (generally ranging between 1:80 and 1:160) of anti-BSA HA antibodies were detected. Thus, in comparison with mice immunized with BSA, animals immunized with R-BSA have very low HA titers (compare FIG. 2A with 2B and FIG. 3A and 3B).

Figure 3B:
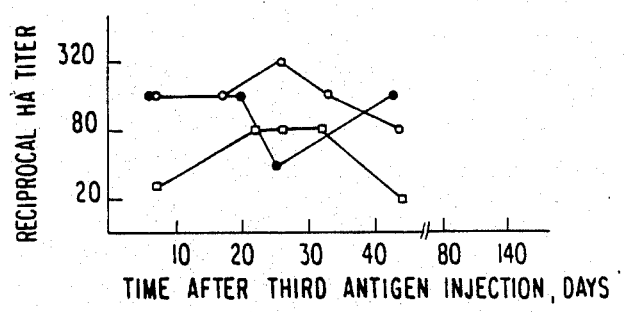

FIG. 3 presents the HA of BSA-HRBC by sera from the individual LAF$_1$ mice immunized by three intradermal injections of BSA or R-BSA. The time of bleeding is indicated on the abscissa taking day 0 as the day when the third injection of antigen was given. The reciprocal of the HA titer is presented on the ordinate. FIG. 3A presents data on mice immunized with BSA: (O) 41.5, F; (●) 41.13, F; (□) 41.25, M; (■) 41.42, M. FIG. 3B presents data on mice immunized with R-BSA: (□) 42.3, F; (O) 42.34, M; (●) 42.37, M.

The findings that TGP can activate several mediator pathways including the activation of factor XII (Hageman factor), the activation of the fibrinolytic system, and the generation of kinins (Becker, C. G., and Dubin, T. (1977) *J. Exp. Med.* 146, 457–467) further emphasize the importance of TGP in the parthogenesis of disease. We thus examined in detail the immune response of mice to TGP.

The immunizing procedures which have been reported to stimulate IgE synthesis in experimental animals generally give rise to relatively transient responses which are down-regulated by suppressor T-cell activity. Levine and Vaz (Levine, B. B., and Vaz, N. M. (1970) *Int. Arch, Allergy Appl. Immunol.* 39, 156–171), using a very low dose of antigen in alum obtained a long-lasting IgE response, the persistence of which appear to depend upon repeated boosting. The immunizing protocol described herein (three intradermal injection of antigen, at monthly intervals, the first in saline and the latter two precipitated on alum) elicits a prolonged IgE response which persists in the absence of further boosting for at least six months. This persistence presumably reflects a failure to stimulate suppressor activity.

It should be noted that some antiserum samples failed to give PCA reactions while samples obtained several days before and after were highly reactive. This is probably a valid observation as all samples which did not give PCA reactions were retested at 1:5 dilution and still did not react. Cycling of antibody concentration, presumably due to a type of "feedback inhibition" by antibody, by anti-idio-type antibody, or by suppressor T cells, has been previously described (Weigle, W. O. (1975) *Adv. Immunol,* 21, 82–111; Kelsoe, G., and Cerny, J. (1979) *Nature* (Lond.) 279, 333–334).

The immunization schedule described above elecits high titered, long-persisting (over six months) IgE and HA antibody responses to BSA. In contrast, when similarly immunized with R-BSA or TGP, mice have a high-titered very long-lasting IgE antibody response but produce little or no HA antibodies. The data show that the presence of rutin groups on the immunizing antigen influences isotype expression by bringing about a depression of the production of isotypes other than IgE such as IgG and IgM.

The low titer of HA antibodies to BSA detected in sera from R-BSA immunized mice is in contrast to the high titer of IgE antibodies to BSA observed in these same sera. The data thus show that the presence of the rutin group on the antigen results in an inhibition of the production of serum antibodies of isotypes other than IgE.

While the invention has been described in detail and with respect to various embodiments thereof, it is apparent that various changes and modifications may be made therein without departing from the spirit and scope thereof.

What is claimed is:

1. A process for the selective immunosuppression of an antibody, which antibody is not of the IgE isotype which comprises:
   (1) coupling a rutin like polyphenol having at least two hydroxyl groups to an antigen which antigen induces the formation of antibodies involved in a disuse or allergic condition to thereby form a resulting product, provided that if only two hydroxyl groups are present in said polyphenol, the hydroxyl groups are in an ortho position to one another and,
   (2) injecting a sufficient amount of said resulting product intradermally into a subject,
   whereby production of said antibody complimentary to said antigen is selectively suppressed 2. A process as in claim 1, wherein said polyphenol is a shikimate derived aromatic, an acetate/shikimate aromatic, or an acetate/malonate aromatic.

3. A process as in claim 1, wherein said antibody is a hemogylutinatiny antibody.

4. A process as in claim 3, wherein said antibody is IgG or IgM.

5. A process as in claim 1, wherein said subject is a subject in need of therapy.

6. A process as in claim 5, wherein said subject is a subject with an immunologically mediated disease, 7. A process for the selective expression of IgE which comprises:
   (1) coupling a rutin like polyphenol having at least two hydroxyl groups to an antigen which antigen induces the formation of antibodies involved in a disease or allergic condition thereby form a resulting product, provided that if only two hydroxyl groups are present in said polyphenol, the hydroxyl groups are in an ortho position to one another, and
   (2) injecting a sufficient amount said resulting product intradermally into a subject,
   whereby production of said IgE complimentary to said antigen is selectively expressed.

8. A process as in claim 7, wherein said polyphenol is a shikimate derived aromatic, an acetate/shikimate aromatic, or an acetate/malonate aromatic.

9. A process as in claim 7, wherein said subject is a subject in need of therapy.

10. A process as in claim 9, wherein said subject is a subject with an immunologically mediated disease.

* * * * *